United States Patent [19]

Preston et al.

[11] 4,085,103

[45] Apr. 18, 1978

[54] 6-SUBSTITUTED-4-HYDROXYCINNOLIN-3-yl-CARBOXYLIC ACIDS AND ESTERS THEREOF

[75] Inventors: John Preston; Austin John Reeve, both of Macclesfield, England

[73] Assignee: Imperial Chemical Industries Limited, London, England

[21] Appl. No.: 794,114

[22] Filed: May 5, 1977

Related U.S. Application Data

[63] Continuation of Ser. No. 626,531, Oct. 28, 1975, Pat. No. 4,045,439.

[30] Foreign Application Priority Data

Nov. 7, 1974 United Kingdom .............. 48205/74

[51] Int. Cl.² ............................................ C07D 237/28
[52] U.S. Cl. ................................................. 260/250 C
[58] Field of Search ..................................... 260/250 C

[56] References Cited

U.S. PATENT DOCUMENTS 2,797,218  6/1957  Barber et al. .................... 260/250 C

FOREIGN PATENT DOCUMENTS

46/22,028  2/1969  Japan.
1,306,839  2/1973  United Kingdom.

OTHER PUBLICATIONS

Barber et al. J. Chem. Soc. (c) 1967, p. 1657.

*Primary Examiner*—R. Gallagher
*Assistant Examiner*—Mark L. Berch
*Attorney, Agent, or Firm*—Cushman, Darby & Cushman

[57] ABSTRACT

6-Dimethylamino-4-hydroxycinnolin-3-yl carboxylic acid; ethyl 6-n-but-2-ylamino-4-hydroxycinnolin-3-yl carboxylate or the pharmaceutically-acceptable acid-addition salts thereof. The compounds are active as inhibitors of effects following the combination of reagin-like antibodies and their antigens.

2 Claims, No Drawings

6-SUBSTITUTED-4-HYDROXYCINNOLIN-3-yl-CARBOXYLIC ACIDS AND ESTERS THEREOF

This is a continuation of appl. Ser. No. 626,531 filed Oct. 28, 1975, now U.S. Pat. No. 4,045,439.

This invention relates to heterocyclic compounds, and more particularly it relates to new cinnoline derivatives which are active as inhibitors of the effects following the combination of reagin-like antibodies and their antigens.

According to the invention there are provided cinnoline derivatives of the formula:

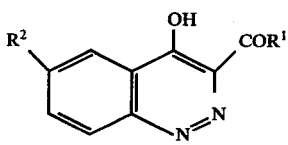

wherein $R^1$ stands for a hydroxy or $C_{1-6}$-alkoxy radical, and $R^2$ stands for a $C_{1-5}$-alkylamino or di-$C_{1-5}$-alkylamino radical, and pharmaceutically-acceptable salts thereof.

It is to be understood that the compounds of the formula I can exist in the tautomeric cinnolone form having the formula:

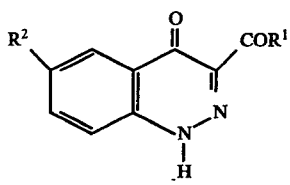

wherein $R^1$ and $R^2$ have the meanings stated above, but for convenience they will all be referred to as 4-hydroxycinnoline derivatives in this specification.

As a suitable value for $R^1$ there may be mentioned, for example, a hydroxy, methoxy or ethoxy radical.

As a suitable value for $R^2$ there may be mentioned, for example, an n-but-2-ylamino or dimethylamino radical.

A sub-group of compounds of the invention which are preferred because of their high oral activity are compounds of the formula I wherein $R^1$ stands for a hydroxy or $C_{1-3}$-alkoxy radical and $R^2$ stands for a $C_{3-5}$—alkylamino radical of the formula alkyl$^1$(alkyl$^2$)CH.NH—wherein alkyl$^1$ and alkyl$^2$ may be the same or different, for example an isopropylamino or n-but-2-ylamino radical, and pharmaceutically-acceptable salts thereof.

Suitable salts of the invention in the case where the compounds of the formula I are sufficiently basic are acid-addition salts derived from inorganic or organic acids affording pharmaceutically-acceptable anions, for example hydrochlorides or citrates. Suitable salts in the case where the compounds of the formula I are sufficiently acidic, for example wherein $R^1$ stands for a hydroxy radical, are salts wherein the anion is derived from the said compound of the formula I and the cation is pharmaceutically-acceptable. Examples of such salts are ammonium, alkali metal, alkaline earth metal or aluminium salts, or a salt with a pharmaceutically-acceptable organic base, for example N-methylglucamine, triethanolamine or 2-amino-2-hydroxy-methyl-1,3-propanediol. These salts are all obtainable by conventional chemical means.

The compounds of the invention are all obtainable by the use of known general chemical processes (i.e. by the use of so-called analogy processes).

Compounds of the formula I wherein $R^1$ has the meaning stated above and $R^2$ stands for an amino radical are obtained by reducing the corresponding compound wherein $R^2$ stands for a nitro group. The reduction may, for example, be carried out by the use of hydrogen and a suitable hydrogenation catalyst, for example palladium-on-charcoal, in the presence of a suitable solvent, for example a $C_{1-5}$-alkanol, for example ethanol.

Compounds of the formula I wherein $R^1$ has the meaning stated above and $R^2$ stands for a dimethylamino radical are obtained by reacting the corresponding compound wherein $R^2$ stands for an amino radical with formaldehyde and formic acid.

Compounds of the formula I wherein $R^1$ has the meaning stated above and $R^2$ stands for a $C_{3-5}$—alkylamino radical of the formula —NHCHR$^3$R$^4$, wherein R$^3$ stands for hydrogen or an alkyl radical and R$^4$ stands for an alkyl radical stands for a cycloalkylamino radical of not more than 6 carbon are obtained by reacting the corresponding compound of the formula I wherein $R^2$ stands for an amino radical with the appropriate carbonyl compound, for example acetone, under reducing conditions. The reducing conditions may be provided by the use of hydrogen and a suitable hydrogenation catalyst, for example a platinum catalyst, or by the use of an alkali metal borohydride.

The above-mentioned biological activity of the compounds of this invention has been demonstrated by their ability to inhibit, in the rat, passive cutaneous anaphylaxis induced by reagin-like antibodies to egg albumin, using *Bordetella pertussis* as an adjuvant. This is a known meaningful test. The activity of individual compounds of this invention in the test depends upon their precise chemical structure, but generally speaking the compounds exhibit activity at an intravenous dose of 0.2 to 20 mg./kg. No toxic effects or undesirable side effects have been observed with the compounds at doses at which they are active in the above-mentioned test. One particularly important feature of the majority of the compounds of the invention is that they are active orally.

When a compound of the invention is used in a warm-blooded mammal, for example man, for the treatment of intrinsic (non-allergic) asthma or a disease or syndrome which is initiated by an antigen-antibody reaction, for example allergic asthma, hay fever, urticaria or an autoimmune disease, it is recommended that the said compound be administered either (a) by inhalation at a dose of 0.01 mg./kg. to 1 mg./kg. at appropriate intervals, for example at 6-hourly intervals during the day, or (b) intravenously at a total daily dose of 25 mg. per man, or (c) orally at a dose of 5 mg./kg. to 250 mg./kg. at appropriate intervals, for example at 6-hourly intervals during the day, or (d) as a suppository at a dose of 5 to 250 mg.

The invention is illustrated but not limited by the following Examples:

EXAMPLE 1

A solution of 6-amino-4-hydroxycinnolin-3-yl carboxylic acid (1.0 g.) in 98% w/v formic acid (2.0 ml.) and 40% w/v formaldehyde in water (2.0 ml.) was heated under reflux on a steam bath for 8 hours. The solution was cooled in ice. The solid which separated was filtered off, washed with methanol and dried to give 6-dimethylamino-4-hydroxycinnolin-3-yl carboxylic acid, m.p. over 330° C.

EXAMPLE 2

A suspension of ethyl 4-hydroxy-6-nitrocinnolin-3-yl carboxylate (2.63 g.) and platinum oxide (100 mg.) in a mixture of dry ethanol (20 ml.), acetone (5 ml.) and glacial acetic acid (1 ml.) was stirred at room temperature in an atmosphere of hydrogen until the uptake of hydrogen ceased. Charcoal (0.5 g.) was added, the mixture was heated under reflux for 10 minutes on a steam bath, filtered through celite and evaporated to dryness in vacuo.

The solid residue was crystallised from aqueous ethanol to give ethyl 4-hydroxy-6-isopropylaminocinnolin-3-yl carboxylate, m.p. 170°–1° C.

EXAMPLES 3

In an analogous manner to that described in Example 2 there was obtained:

ethyl 6-n-but-2-ylamino-4-hydroxycinnolin-3-yl carboxylate, m.p. 169° C.

What we claim is:

1. 6-Dimethylamino-4-hydroxycinnolin-3-yl carboxylic acid or a pharmaceutically-acceptable salt thereof.
2. Ethyl 6-n-but-2-ylamino-4-hydroxycinnolin-3-yl carboxylate or a pharmaceutically-acceptable acid-addition salt thereof.

* * * * *